United States Patent
Corradi (10) Patent No.: US 8,697,928 B2
(45) Date of Patent: Apr. 15, 2014

(54) PROCESS AND APPARATUS FOR PARA-XYLENE PRODUCTION USING MULTIPLE ADSORPTIVE SEPARATION UNITS

(75) Inventor: Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/326,906

(22) Filed: Dec. 15, 2011

(65) Prior Publication Data
US 2013/0158334 A1    Jun. 20, 2013

(51) Int. Cl.
C07C 5/27    (2006.01)
C07C 7/12    (2006.01)

(52) U.S. Cl.
USPC .................. 585/478; 585/477; 585/828

(58) Field of Classification Search
None
See application file for complete search history.

(56) References Cited

U.S. PATENT DOCUMENTS

| | | | |
|---|---|---|---|
| 4,039,599 A | 8/1977 | Gewartowski | |
| 7,683,233 B2 * | 3/2010 | Ou et al. | 585/828 |
| 7,687,674 B2 | 3/2010 | Wegerer | |
| 7,915,471 B2 | 3/2011 | Leflaive et al. | |
| 7,977,526 B2 | 7/2011 | Porter | |
| 8,008,536 B2 | 8/2011 | Winter et al. | |
| 8,273,934 B2 * | 9/2012 | Ou et al. | 585/478 |
| 2007/0249882 A1 * | 10/2007 | Ou et al. | 585/478 |
| 2009/0069612 A1 | 3/2009 | Hotier et al. | |
| 2010/0305381 A1 * | 12/2010 | Go et al. | 585/826 |

OTHER PUBLICATIONS

Lacosse, et al., BTX production: Flexibility through modern UOP Technology, Hydrocarbon Technology International, 125-28, 1993.
D'Auria, et al., Produce para-xylene economically, Chem Systems Annual US Chemical Conference (Houston Jan. 29-30, 1997), Fuel Technology & Management, 7 (3): 35-36,38,40-41, 1997.
Basak, Aromatics & Down Stream Process, GM(PC), IOCL-RHQ, IndianOil.

* cited by examiner

*Primary Examiner* — Tam M Nguyen
(74) *Attorney, Agent, or Firm* — Mark R Willis (57) ABSTRACT

A process for separating para-xylene from a plurality of aromatic compounds, wherein the process introduces a mixed xylene feed stream comprising a plurality of xylene isomers into a first separation assembly to produce a first para-xylene enriched stream and a first raffinate stream. The process further feeds the raffinate stream into an isomerization unit to convert the raffinate stream into an isomerization reactor product stream, and introduces the isomerization reactor product stream into to a second para-xylene adsorptive separation unit to produce a second para-xylene enriched stream and a second raffinate stream.

17 Claims, 3 Drawing Sheets

Fig. 1

PRIOR ART

PROCESS AND APPARATUS FOR PARA-XYLENE PRODUCTION USING MULTIPLE ADSORPTIVE SEPARATION UNITS

FIELD OF THE INVENTION

The disclosure relates to a process for the formation and adsorptive separation of a select xylene isomer, preferably para-xylene, from a feed stream containing a mix of aromatic and non-aromatic hydrocarbons. More specifically, the disclosure relates to increasing the efficiency of para-xylene production by eliminating the need to vaporize the product stream from the isomerization process. Most specifically, the disclosure relates to a para-xylene process comprising multiple adsorptive separation units, each using a different desorbent, to eliminate fractional distillation of the isomerized product stream.

BACKGROUND OF THE INVENTION

Para-xylene, an aromatic hydrocarbon, is an important intermediate which finds wide and varied application in chemical syntheses. Upon oxidation, para-xylene yields terephthalic acid. Polyester fabrics and resins are produced from a polymer of ethylene glycol and terephthalic acid. These polyester materials are used extensively in a number of industries and are used to manufacture such items as, for example, clothing, beverage containers, electronic components, and insulating materials.

The production of para-xylene is practiced commercially in large-scale facilities and is highly competitive. Concerns exist not only about the effective conversion of feedstock through one or more of isomerization, transalkylation and disproportionation to produce para-xylene, and effective separation of para-xylene from the resultant mixture of C8 aromatic isomers, but also with the energy costs and capital costs associated with such processes.

In prior art processes, C9 aromatics are separated from C8 aromatics, i.e. xylenes and ethylbenzene, by fractional distillation. This requires heating of the admixture to vaporize the C8 and lighter aromatics. An isomerization stream must be vaporized to accomplish the C9 separation because the stream is generally composed primarily of C8 and lighter aromatics. This separation requires a substantial amount of energy and associated cost.

Accordingly, it would be an advance in the state of the art to provide a process for the production of para-xylene, including separation and isomeric formation from an admixture of C8 aromatic isomers, that removes the need to vaporize an isomerized stream for removal of C9 aromatics, thereby lowering the energy consumption requirements and/or size of the processing equipment.

SUMMARY OF THE INVENTION

A process for separating para-xylene from a plurality of aromatic compounds is presented. The process introduces a mixed xylene stream comprising a plurality of xylene isomers into a first separation assembly, and produces a first para-xylene enriched stream and a first raffinate stream. The process then introduces the first raffinate stream into an isomerization unit to convert the first raffinate stream into an isomerization reactor product stream. The process further introduces the isomerization reactor product stream into a second separation assembly and produces a second para-xylene enriched stream and a second raffinate stream.

An apparatus for separating para-xylene from a plurality of aromatic compounds is presented. The apparatus comprises a first separation assembly comprising a first adsorptive separation unit, a second separation assembly comprising a second adsorptive separation unit, and an isomerization unit in fluid communication with both the first separation assembly and the second separation assembly.

DETAILED DESCRIPTION OF PREFERRED EMBODIMENTS

Para-xylene is typically recovered from a mixed aromatic hydrocarbon fraction derived from various sources such as catalytic reforming by liquid-liquid extraction and/or fractional distillation. The para-xylene is commercially separated from a feed stream that typically contains all three xylene isomers, namely ortho-xylene, meta-xylene, and para-xylene. The para-xylene, or other desired isomer, is separated by either fractional crystallization or adsorptive separation or a combination of these two techniques. Adsorptive separation is generally preferred as it has a significantly higher single pass recovery (~97%) relative to crystallization separation (~65%).

A typical adsorptive separation process first involves the separation of C8 aromatic hydrocarbons, including ortho-xylene, meta-xylene, para-xylene, and ethylbenzene, from heavier aromatic hydrocarbons (i.e., C9+) and non-aromatic hydrocarbons through fractional distillation.

Those skilled in the art will appreciate that the designator "CX" refers to a compound comprising X carbon atoms, "CX+" refers to a compound comprising X or greater carbon atoms, and "CX−" refers to a compound comprising X or fewer carbon atoms.

The para-xylene isomers are then separated from the C8 isomer admixture using a simulated countercurrent moving-bed (SMB) adsorptive separation unit. This simulation is performed using established commercial technology wherein an adsorbent, commonly a solid zeolitic material, is held in place in one or more cylindrical adsorbent chambers. The positions at which the streams involved in the process enter and leave the chamber(s) are slowly shifted along the height of the chamber(s). Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals in a step-wise manner. Each shift in location of these transfer points delivers or removes liquid from a different bed within the chamber.

A typical chamber has a single line for each bed. The flow into or out of a particular line, as the case may be, is controlled by a rotary valve. The shifting of streams along the bed simulates movement of the adsorbent in a direction opposite the flow of liquid, even though the adsorbent is fixed in place within the chamber. SMB chambers are also well suited for high volume production because the input and output streams have nearly constant compositions throughout simulated motion of the adsorbent material in the bed.

A typical SMB unit recycles a heavy desorbent, such as para-diethylbenzene, to separate high purity para-xylene from the other C8 isomers. Para-diethylbenzene is a C10 aromatic that is separated from para-xylene by fractional distillation.

The admixture of non-para-xylene isomers from the adsorptive separation unit is subjected to catalytic isomerization to reestablish an equilibrium amount of para-xylene isomers in the admixture. In addition to para-xylene and other C8 isomers, the isomerized stream typically contains an amount of C9+ aromatics, which will accumulate in the desorbent and, therefore, must be removed.

Processes for isolating a desired isomer of xylene without the vaporization of the full isomerized product stream are presented. The process comprises two adsorptive separation units. The first unit utilizes a heavy desorbent and the second unit utilizes a light desorbent. Those skilled in the art will appreciate that a desorbent used in combination with a simulated moving bed adsorbent system facilitates removal of an adsorbed material from the adsorbent bed. This being the case, a useful desorbent will have an affinity for the desired material, i.e. para-xylene, that is substantially the same as the affinity of the adsorbent bed for that desired material.

As used herein, the terms heavy and light are generally in reference to the boiling point of the desorbent relative to the C8 aromatics, namely, ortho-, meta-, para-xylene and ethylbenzene.

In certain embodiments, the heavy desorbent is selected from the group consisting of para-diethylbenzene, para-diisopropylbenzene, tetralin, and the like, and combinations thereof. In certain embodiments, toluene and the like can be used as the light desorbent. The para-diethylbenzene has a higher boiling point than the C8 aromatic isomers and, as such, the para-diethylbenzene is the bottoms (i.e., heavy) product when separated from the C8 isomers in a fractional distillation column. Similarly, toluene has a lower boiling point than the C8 aromatic isomers and, as such, the toluene is the overhead (i.e., light) product when separated from the C8 isomers in a fractional distillation column.

Unlike prior art processes, Applicant's process comprises feeding a stream of material containing a desired xylene isomer formed in an isomerization unit into a second adsorptive separation unit, as opposed to being fed back into a fractional distillation column. An extract stream from the second adsorptive separation unit, rich in the desired xylene isomer, is fed back into a first adsorptive separation unit for isolation of the desired xylene isomer. The process is presented in greater detailed below.

Figure 1:
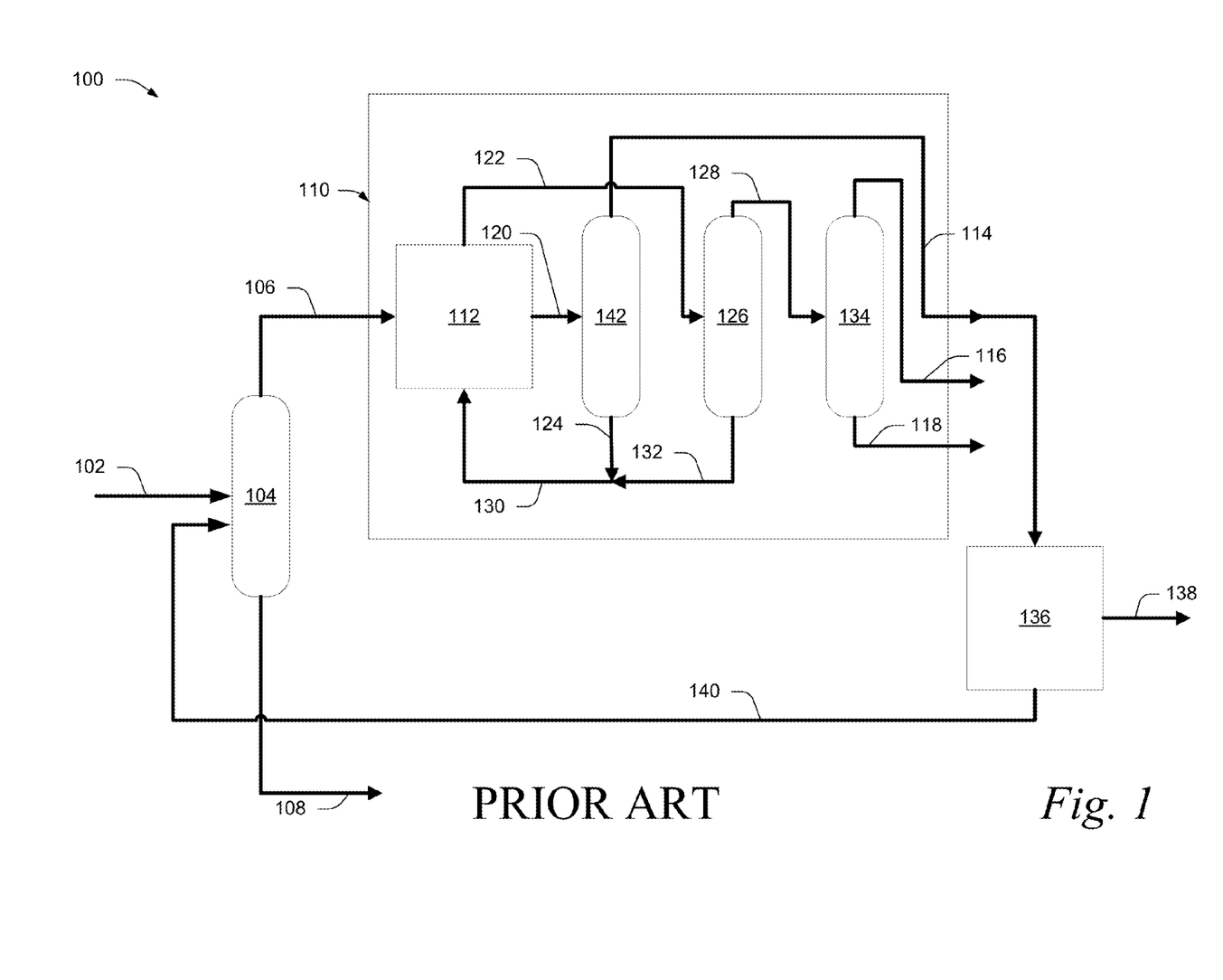
FIG. 1 is a diagram of a prior art process.

Referring to FIG. 1, a diagram 100 of a prior art process for the production of para-xylene is depicted. A feed stream 102 enters a xylene fractionation unit 104. The feed stream typically contains ortho-, meta-, and para-xylene isomers and may also contain quantities of ethylbenzene, toluene, C8 cycloalkanes, alkanes, and hydrocarbons having more than eight carbon atoms per molecule.

The xylene fractionation unit 104 is a fractional distillation column. The xylene fractionation unit 104 divides the incoming stream into an overhead stream 106 comprising the C8 and lighter aromatics, including the xylene isomers, ethylbenzene, and toluene, and a bottoms 108 and one or more side cut streams (not shown) comprising C9+ aromatics.

Table 1 recites an example composition for feed stream 102.

TABLE 1

| Component | Amount |
|---|---|
| para-xylene | 10-20 wt % |
| Total C8 Aromatics | 25-60 wt % |
| ethylbenzene | 10-20 wt % |
| toluene | 0.5-2.0 wt % |
| C9+ | 25-30 wt % |
| Nonaromatic hydrocarbons | <0.5 wt % |
| Nitrogen | 1.0 mg/kg |
| Sulfur | 1.0 mg/kg |

The overhead stream 106 enters the separation assembly 110, where the input stream 106 is separated into a raffinate stream 114, a toluene stream 116, and a para-xylene stream 118. The raffinate stream 114 has been substantially depleted of para-xylene but contains other C8 aromatics, including ortho-xylene, meta-xylene and ethylbenzene.

Within the separation assembly 110, the stream 106 enters an adsorptive separation unit 112. The adsorptive separation unit 112 separates the incoming stream 106 into a raffinate stream 120 and an extract stream 122. The adsorptive separation unit 112 typically comprises two SMB chambers and a rotary valve. Each individual chamber typically has 12 beds. A bedline connects each bed to the rotary valve. The rotary valve controls the flow of material into or out of each SMB chamber in a step-wise manner to create a simulated moving bed.

A heavy desorbent, typically para-diethylbenzene, is used to facilitate the separation of the raffinate stream 120 and extract stream 122. The raffinate stream 120 comprises ethylbenzene, meta-xylene, and ortho-xylene diluted with desorbent and any heavies. Heavies are hydrocarbons with a boiling point greater than that of the C8 aromatic isomers and include C9+ aromatics. The extract stream 122 comprises para-xylene diluted with desorbent and light ends. Light ends are hydrocarbons with a boiling point below that of the C8 aromatic isomers and include toluene and other C7− aromatics.

The raffinate stream 120 is directed to a raffinate column 142. The raffinate column 142 is a fractional distillation column that divides the incoming stream 120 into (i) an overhead raffinate stream 114 comprising ethylbenzene, meta-xylene, and ortho-xylene and (ii) a bottoms stream 124 comprising desorbent and any heavies. The bottoms stream 124 is recycled back to the adsorptive separation unit 112 through combined stream 130. The overhead raffinate stream 114 is directed to an isomerization unit 136.

The extract stream 122, comprising xylene isomers and ethylbenzene, enters extract column 126. Extract column 126 is a fractional distillation column that divides the incoming stream 122 into (i) an overhead stream 128 comprising para-xylene and toluene and (ii) a bottoms stream 132 comprising desorbent and heavies. The bottoms stream 132 containing desorbent is recycled back to the adsorptive separation unit 112 through combined stream 130. Heavies in the combined desorbent stream 130 may be removed by directing a slipstream of the desorbent into a small desorbent rerun column.

The overhead stream 128, comprising para-xylene and toluene, enters finishing column 134. Finishing column 134 is a fractional distillation column that divides the incoming stream 128 into (i) an overhead toluene stream 116 and (ii) a bottoms para-xylene stream 118. The bottoms para-xylene stream 118 contains the final desired product.

The raffinate stream 114 comprising ethylbenzene, meta-xylene, and ortho-xylene enters an isomerization unit 136.

Catalysts in the isomerization unit 136 reestablish an equilibrium mixture of the ortho-, meta-, and para-xylene isomers and convert the ethylbenzene into xylenes and/or benzene.

Nonaromatic compounds in the raffinate stream 114 are cracked to light ends and removed in stream 138 along with any benzene. The isomerization process also creates quantities of C9 and heavier aromatics. The output stream 140 comprises an equilibrium mixture of xylene isomers as well as quantities of C9 aromatics and unreacted ethylbenzene. The output stream 140 is recycled back into the xylene fractionation unit 104.

The C9 aromatics produced during isomerization are separated from the C8 isomers in the xylene fractionation unit 104. While the C9+ aromatics are only a very small portion of the stream, the entire C8 fraction must be vaporized to accomplish this separation.

Figure 2:
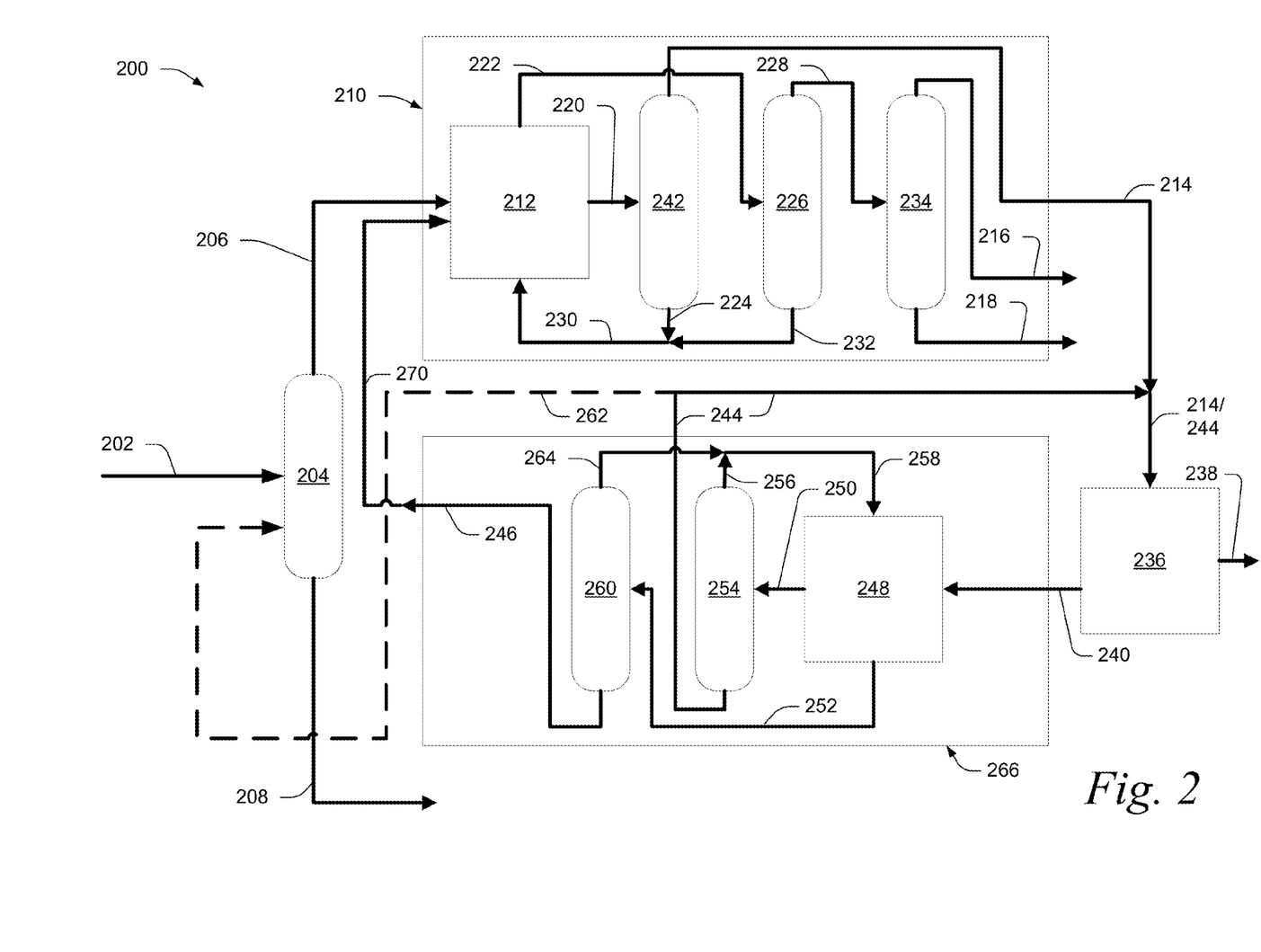
FIG. 2 is a diagram of one embodiment of the disclosed process where a drag stream is fed into the xylene fractionation column.

Referring to FIG. 2, diagram 200 illustrates a first embodiment of Applicant's apparatus and process. A feed stream 202 enters a xylene fractionation unit 204. The feed stream contains ortho-, meta-, and para-xylene isomers and may also contain quantities of ethylbenzene, toluene, C8 cycloalkanes, alkanes, and hydrocarbons having more than eight carbon atoms per molecule.

In one embodiment, the feed stream 202 is a result of hydrotreating naphtha to remove any sulfur and nitrogen contaminants and the subsequent catalytic reforming where paraffins and naphthenes in the decontaminated naphtha are converted to aromatics. Most of the light ends and C7− fractions are removed in a debutanizer and fractional distillation column, respectively. The feed stream 202, comprising a C8+ fraction, enters the xylene fractionation unit 204. In one embodiment, the feed stream 202 comprises about 23 weight percent para-xylene. In one embodiment, the feed stream 202 comprises less than about 23 weight percent para-xylene. In one embodiment, the feed stream 202 comprises more than about 23 weight percent para-xylene.

The xylene fractionation unit 204 is a fractional distillation column. The xylene fractionation unit 204 divides the incoming stream into an overhead stream 206 comprising the C8− aromatics, including the xylene isomers, ethylbenzene, and toluene, and a bottoms stream 208 and one or more side cut streams (not shown) comprising C9+ aromatics.

The overhead stream 206 enters a first separation assembly 210, where input stream 206 is separated into a raffinate stream 214, a toluene stream 216, and a para-xylene product stream 218. The raffinate stream 214 has been substantially depleted of para-xylene but comprises other C8 aromatic isomers, including ortho-xylene, meta-xylene and ethylbenzene. In one embodiment, the toluene stream 216 comprises high purity toluene and any light ends. The para-xylene product stream 218 comprises high purity para-xylene.

Within the first separation assembly 210, input stream 206 enters an adsorptive separation unit 212. The adsorptive separation unit 212 separates the incoming stream 206 into a raffinate stream 220 and an extract stream 222. The raffinate stream 220 comprises ethylbenzene, meta-xylene, and ortho-xylene diluted with desorbent. The extract stream 222 comprises para-xylene diluted with desorbent and toluene.

In one embodiment, adsorptive separation unit 212 comprises an SMB assembly and a rotary valve. In other embodiments, the adsorption separation unit 212 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of the SMB assembly in a step-wise manner to create a simulated moving bed and to flush the bed lines between flows of differing materials.

As a mixture of xylene isomers is fed into adsorptive separation unit 212, and flows downwardly, the mixture of xylene isomers contacts a solid adsorbent within the chamber. The zeolitic adsorbents disposed in adsorptive separation unit 212 have an affinity for para-xylene. As the mixture of xylene isomers flows over the solid adsorbent, the para-xylene is selectively adsorbed into the adsorbent while the other isomers continue to travel downward in the chamber in the bulk liquid.

In one embodiment, the heavy desorbent para-diethylbenzene is used to facilitate the separation of the raffinate stream 220 and extract stream 222. In certain embodiments, the heavy desorbent is selected from the group consisting of para-diethylbenzene, para-diisopropylbenzene, tetralin, and the like, and combinations thereof.

The raffinate stream 220 enters a raffinate column 242. The raffinate column 242 is a fractional distillation column that divides the incoming stream 220 into (i) an overhead raffinate stream 214 comprising ethylbenzene, meta-xylene, and ortho-xylene and (ii) a bottoms stream 224 comprising desorbent and any heavies. The bottoms stream 224 is recycled back to the adsorptive separation unit 212 through combined stream 230.

The extract stream 222, comprising xylene isomers and ethylbenzene, enters extract column 226. Extract column 226 is a fractional distillation column that divides the incoming stream 222 into (i) an overhead stream 228 comprising para-xylene and toluene and (ii) a bottoms stream 232 comprising desorbent and any heavies. The bottoms stream 232 containing desorbent is recycled back to the adsorptive separation unit 212 through combined stream 230.

Any C9+ aromatics or other heavies introduced in the feed 202 and making their way into overhead stream 206 will accumulate in the desorbent recycle loop 230, 220, 222, 224, 232. In one embodiment, to prevent such accumulation, a drag stream (not shown in FIG. 2) is withdrawn from the desorbent loop and run through a fractionating column to strip out any heavies from the desorbent. The overhead raffinate stream 214 is directed to an isomerization unit 236.

The overhead stream 228, comprising para-xylene and toluene, enters finishing column 234. Finishing column 234 is a fractional distillation column that divides the incoming stream 228 into (i) an overhead toluene stream 216 and (ii) a bottoms para-xylene stream 218. In one embodiment, the bottoms para-xylene stream 218 comprises about 98.0 weight percent para-xylene. In one embodiment, the bottoms para-xylene stream 218 comprises about 99.2 weight percent para-xylene. In one embodiment, the bottoms para-xylene stream 218 comprises about 99.7 weight percent para-xylene. In one embodiment, the bottoms para-xylene stream 218 comprises about 99.9 weight percent para-xylene. In one embodiment, the bottoms para-xylene stream 218 comprises greater than about 99.9 weight percent para-xylene.

The raffinate stream 214 comprising ethylbenzene, meta-xylene, and ortho-xylene enters an isomerization unit 236. Catalysts in the isomerization unit 236 reestablish an equilibrium mixture of the ortho-, meta-, and para-xylene isomers. In one embodiment, the catalyst is an ethylbenzene dealkylation catalyst, which converts ethylbenzene to a benzene co-product. In one embodiment, the catalyst is an ethylbenzene isomerization catalyst, which converts the ethylbenzene into additional xylene isomers.

Nonaromatic compounds in the raffinate stream 214 are cracked to light ends and removed in stream 238 along with any benzene co-product created and any excess toluene. The isomerization process may also create small quantities of C9 and heavier aromatics. In one embodiment, the output stream 240 comprises an equilibrium mixture of xylene isomers. In one embodiment, the output stream 240 comprises small quantities of C9+ aromatics. In one embodiment, the output stream 240 comprises unreacted ethylbenzene. In one embodiment, the output stream 240 comprises about 1.5 weight percent ethylbenzene or less.

The isomerization unit output stream 240 enters a second separation assembly 266. The second separation assembly 266 separates input stream 240 into an extract stream 246 and a raffinate stream 244. In one embodiment, the light desorbent toluene is used to facilitate the separation of the raffinate stream 244 and extract stream 246. In another embodiment, a light desorbent other than toluene is used to facilitate the separation of the raffinate stream 224 and extract stream 246.

In one embodiment, the extract stream 246 comprises about 90 weight percent para-xylene. In one embodiment, the extract stream 246 comprises about 95 weight percent para-xylene. In one embodiment, the extract stream 246 comprises greater than about 95 percent para-xylene. In one embodiment, about 90 percent of the para-xylene present in stream 240 is recovered in the extract stream 246. In one embodiment, about 95 percent of the para-xylene present in stream 240 is recovered in the extract stream 246. In one embodiment, greater than about 95 percent of the para-xylene present in stream 240 is recovered in the extract stream 246. In one embodiment, the extract stream 246 comprises a quantity of para-ethyltoluene. In one embodiment, the raffinate stream 244 comprises ortho-xylene and meta-xylene as well as quantities of C7-hydrocarbons, C9 aromatics and other heavies.

Within the separation assembly 266, the stream 240 enters an adsorptive separation unit 248. The adsorptive separation unit 248 separates the incoming stream 240 into a raffinate stream 250 and an extract stream 252. The extract stream 252 comprises para-xylene diluted with desorbent. The raffinate stream 250 comprises ethylbenzene, meta-xylene, and ortho-xylene diluted with desorbent. In one embodiment, the raffinate stream 250 also contains small quantities of C9 aromatic isomers.

In one embodiment, adsorptive separation unit 248 comprises an SMB assembly and a rotary valve. In other embodiments, the adsorption separation unit 212 comprises an SMB assembly and one or more rotary valves, one or more computing device operated valves, or a combination thereof. In one embodiment, the SMB assembly comprises a single physical chamber. In one embodiment, the physical chamber includes 24 beds. In one embodiment, the physical chamber includes less than 24 beds. In one embodiment, the SMB assembly includes two physical chambers. In one embodiment, each physical chamber includes 12 beds. In one embodiment, each physical chamber includes less than 12 beds. In one embodiment, each physical chamber includes more than 12 beds. In one embodiment, the physical chambers have an unequal number of beds. A bed line connects each bed in the SMB assembly to the rotary valve. The rotary valve controls the flow of material into or out of each SMB assembly in a step-wise manner to create a simulated moving bed and to flush the bed lines between flows of differing materials.

As a mixture of xylene isomers is fed into adsorptive separation unit 248, and flows downwardly, the mixture of xylene isomers contacts a solid adsorbent within the chamber. The zeolitic adsorbents disposed in adsorptive separation unit 248 have an affinity for para-xylene. As the mixture of xylene isomers flows over the solid adsorbent, the para-xylene is selectively adsorbed into the adsorbent while the other isomers continue to travel downward in the chamber in the bulk liquid.

The raffinate stream 250 enters raffinate column 254. The raffinate column 254 is a fractional distillation column that divides the incoming stream 250 into (i) an overhead stream 256 comprising desorbent and (ii) a bottoms raffinate stream 244. The overhead stream 256 is recycled back to the adsorptive separation unit 248 through combined stream 258. The bottoms raffinate stream 244, comprising ortho-xylene, meta-xylene, and ethylbenzene, exits the separation assembly 266.

The extract stream 252 enters extract column 260. The extract stream 252 comprises para-xylene diluted with desorbent. In one embodiment, the extract stream 252 comprises a quantity of C9 aromatic isomers. Extract column 260 is a fractional distillation column that divides the incoming stream 252 into (i) the overhead stream 264 comprising desorbent and (ii) a bottoms extract stream 246 comprising a high weight percentage of para-xylene. The overhead stream 264 is recycled back to the adsorptive separation unit 248 through combined stream 258. The bottoms extract stream 246 exits the separation assembly 266.

The extract stream 246 from the second separation assembly 266 is introduced into the first separation assembly 210 by way of stream 270. In some embodiments, the para-xylene present in stream 246 is high in para-xylene content, but also contains a small quantity of C9 aromatics, such as para-ethyltoluene. Para-ethyltoluene, structurally similar to para-xylene, may be introduced into the process by the isomerization unit 236.

The apparatus and process of FIG. 2, unlike the prior art apparatus and process of FIG. 1, utilizes two adsorptive separation units 212 and 248 but only a single finishing column 234. The finishing column 234 in the first separation assembly 210 removes toluene and light ends (C7− aromatics) present in the incoming feed 202 to obtain a high purity para-xylene product. In comparison, the second separation assembly 266 does not include a finishing column. Instead, the extract stream 246 is fed into the first separation assembly 210 and eventually flows through finishing column 234, which removes any light ends. As such, the single finishing column 234 serves to purify the final para-xylene product.

In one embodiment, the first separation assembly 210 uses a heavy desorbent, para-diethylbenzene, to extract the para-xylene. The para-diethylbenzene is then separated from the para-xylene in the extract column 226 for recirculation back into the SMB chambers via stream 232. In comparison, in one embodiment, the second separation assembly 266 uses a light desorbent, toluene, to extract the para-xylene. Practically all toluene contained in the original feed stream 202 is removed in the first separation unit 210 as stream 216. As such, the stream feeding the second separation assembly 266 introduces little or no additional toluene to build up in the desorbent loop (i.e., 252, 250, 264, 256, and 258). In one embodiment, any excess toluene in the desorbent loop is removed in stream 238. In certain embodiments, a heavy desorbent other than para-diethylbenzene is used in the first separation assembly 210 and a light desorbent other than toluene is used in the second separation assembly 266.

In certain embodiments, certain C9+ aromatics that may be introduced in isomerization unit 236 will accumulate in a first isomerization loop 214, 240, 244. In one embodiment, to prevent such accumulation, a drag stream 262 is withdrawn from the raffinate stream 244 and fed into the xylene fractionation unit 204 in a continuous manner. In one embodiment, the amount of material in the drag stream 262 is about 1 to about 20 volume percent of the bottoms raffinate stream 244.

In one embodiment, a drag stream 262 is withdrawn from the raffinate stream 244 and fed into the xylene fractionation unit 204 periodically as the accumulation of heavies impedes the ability of the xylene adsorptive separation unit 248 to separate para-xylene from the other xylene isomers. At other times, no material flows through the drag stream 262. The C9+ aromatics and other heavies are then removed in bottoms stream 208. In other embodiments, the accumulation of heavies in the first isomerization loop is prevented using another technique known in the art capable of separating heavies from a stream of C8 aromatic isomers.

Figure 3:
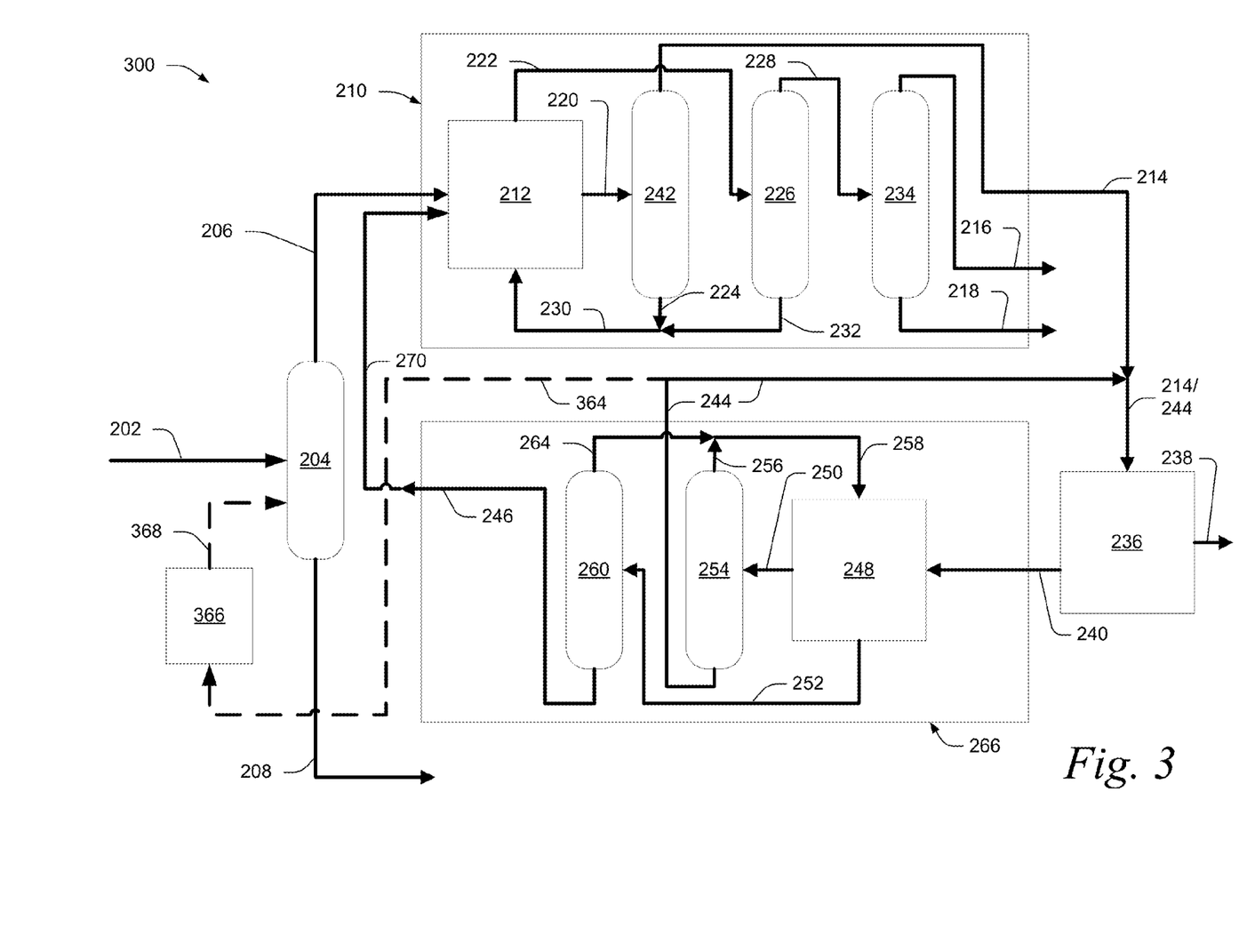
FIG. 3 is a diagram of one embodiment of the disclosed process where a drag stream is fed into an aromatic conversion unit.

Referring to FIG. 3, a diagram 300 of one embodiment of Applicant's process is depicted. The build-up of heavies in the isomerization loop are removed by withdrawing a drag stream 364 from the raffinate stream 244 of the second separation assembly 266 and feeding the drag stream into an aromatic conversion process 366. In one embodiment, the material flows in the drag stream in a continuous manner. In one embodiment, the amount of material in the drag stream 364 is about 1 to about 20 volume percent of the bottoms raffinate stream 244. In one embodiment, a drag stream 364 is withdrawn from the raffinate stream 244 and fed into the aromatic conversion unit 366 periodically as the accumulation of heavies impede the ability of the xylene adsorptive separation unit 248 to separate para-xylene from the other xylene isomers.

The aromatic conversion unit 366 converts the incoming stream 364 comprising C9+ aromatics into an output stream 368 comprising xylenes and benzene. In one embodiment, the stream 368 is then fed back into the xylene fractionation unit 204.

The apparatus and process of FIGS. 2 and 3 provide a number of improvements over the prior art apparatus and process of FIG. 1. The energy required by the xylene fractionation unit 204 in the process of diagrams 200 and 300 is less than one half of the energy of the prior art process, for the same initial feed stream. As a result, the process of diagrams 200 and 300 each require less energy to operate the xylene fractionation unit. This energy savings comes as a result of eliminating the need to vaporize the entire isomerized stream 240. Instead, the isomerized stream 240 is treated with a second separation assembly 266 using a light desorbent, wherein the output streams 244 and 246 of the second separation assembly 266 are recycled into the process downstream of the xylene fractionation unit. In one embodiment, only a small portion of the material in the isomerized stream 240 is vaporized in the xylene fractionation unit 204 by way of drag streams 262 and 364. In another embodiment, the drag stream is not recycled back into the process. In another embodiment, the process of diagram 200 and 300 does not include a drag stream because the introduction of heavies into the process is limited by other techniques.

In one embodiment, the total feed rate into the xylene adsorptive separation unit 212 for the process in diagrams 200 and 300, by way of 202 and 262/368, is less than one half of that of the process in diagram 100. In one embodiment, the para-xylene concentration (in weight percent) into the xylene adsorptive separation unit 212 for the process in diagrams 200 and 300 is over double of that of the process in diagram 100. In one embodiment, the ethylbenzene concentration into the second separation assembly 266 is about 1.5 weight percent. As a result, the xylene fractionation unit 204, raffinate column 242 and SMB chambers within the adsorptive separation unit 212 may be smaller, as compared to the prior art process in diagram 100, for the same initial feedstock feed rate.

Referring to the foregoing paragraphs, this invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

While the invention is described through the above-described exemplary embodiments, it will be understood by those of ordinary skill in the art that modifications to, and variations of, the illustrated embodiments may be made without departing from the inventive concepts disclosed herein. For example, although some aspects of separating para-xylene has been described, those skilled in the art should readily appreciate that functions, operations, decisions, etc., of all or a portion of each step, or a combination of steps, of the series of steps described may be combined, separated into separate operations or performed in other orders. Moreover, while the embodiments are described in connection with various illustrative processes, one skilled in the art will recognize that the methods and processes described herein can be embodied using a variety of techniques. Furthermore, disclosed aspects, or portions of these aspects, may be combined in ways not listed above. Accordingly, the invention should not be viewed as being limited to the disclosed embodiment(s). The scope of the invention should be determined with reference to the pending claims along with their full scope or equivalents, and all changes which come within the meaning and range of equivalency of the claims are to be embraced within their full scope.

What is claimed is:

1. A process for separating para-xylene from a plurality of aromatic compounds, the process comprising:

feeding a first mixed aromatic feed stream comprising a plurality of aromatic compounds into a xylene fractionation unit to produce a mixed xylene stream;

introducing the mixed xylene stream comprising a plurality of xylene isomers into a first separation assembly and producing a first para-xylene enriched stream and a first raffinate stream;

feeding said first raffinate stream into an isomerization unit to convert said first raffinate stream into an isomerization reactor product stream;

introducing the isomerization reactor product stream into a second separation assembly and producing a second para-xylene enriched stream and a second raffinate stream;

introducing the second para-xylene enriched stream into the first separation assembly while bypassing the xylene fractionation unit; and deriving a drag stream from the second raffinate stream for fluid communication to the xylene fractionation unit.

2. The process of claim 1, wherein:

said introducing the mixed xylene stream comprises introducing the mixed xylene stream and a first desorbent stream into a first adsorptive separation unit disposed within the first separation assembly; and said introducing the isomerization reactor product stream comprises introducing the isomerization reactor product stream and a second desorbent stream into a second adsorptive separation unit disposed within the second separation assembly.

3. The process of claim 2, wherein the first desorbent stream differs from the second desorbent stream.

4. The process of claim 3, wherein:

the first desorbent stream comprises a desorbent selected from the group consisting of para-diethylbenzene, para-diisopropylbenzene, and tetralin; and the second desorbent stream comprises toluene.

5. The process of claim 1, wherein the isomerization reactor product stream is not introduced into the xylene fractionation unit.

6. The process of claim 1, wherein introducing the second para-xylene enriched stream comprises introducing the second para-xylene enriched stream into a first adsorptive separation unit.

7. The process of claim 1, further comprising introducing the drag stream derived from the second raffinate stream directly into the xylene fractionation unit.

8. The process of claim 1, further comprising:

introducing the drag stream derived from the second raffinate stream into an aromatic conversion unit and producing a second mixed aromatic stream; and introducing the second mixed aromatic stream into the xylene fractionation unit.

9. A process for separating para-xylene from a plurality of aromatic compounds, the process comprising:

feeding a first mixed aromatic feed stream comprising a plurality of aromatic compounds into a xylene fractionation unit to produce a mixed xylene stream;

introducing the mixed xylene stream comprising a plurality of xylene isomers into a first separation assembly and producing a first para-xylene enriched stream and a first raffinate stream;

feeding the first raffinate stream into an isomerization unit to convert the first raffinate stream into an isomerization reactor product stream;

introducing the isomerization reactor product stream into a second separation assembly and producing a second para-xylene enriched stream and a second raffinate stream;

introducing all of the second para-xylene enriched stream into the first separation assembly while bypassing the xylene fractionation unit; and deriving a drag stream from the second raffinate stream for fluid communication to the xylene fractionation unit.

10. The process of claim 9 wherein:

introducing the mixed xylene stream comprising a plurality of xylene isomers into the first separation assembly and producing the first para-xylene enriched stream and the first raffinate stream comprises introducing the mixed xylene stream comprising the plurality of xylene isomers into the first separation assembly including a first adsorptive separation unit comprising a finishing column; and introducing the isomerization reactor product stream into the second separation assembly and producing the second para-xylene enriched stream and the second raffinate stream comprises introducing the isomerization reactor product stream into the second separation assembly including a second adsorptive separation unit lacking a finishing column.

11. The process of claim 10 wherein:

feeding the first raffinate stream into the isomerization unit to convert the first raffinate stream into the isomerization reactor product stream comprises feeding the first raffinate stream directly from the first separation assembly into the isomerization unit; and introducing all of the second para-xylene enriched stream into the first separation assembly comprises feeding the second para-xylene enriched stream directly from the second separation assembly into the first separation assembly.

12. The process of claim 11 further comprising:

dividing the second raffinate stream into a first portion as the drag stream and a second portion;

introducing the first portion of the second raffinate stream into an aromatic conversion unit and producing a second mixed aromatic stream;

introducing the second mixed aromatic stream into the xylene fractionation unit; and introducing the second portion of the second raffinate stream into the isomerization unit.

13. The process of claim 9 wherein introducing the mixed xylene stream comprising the plurality of xylene isomers into the first separation assembly and producing the first para-xylene enriched stream and the first raffinate stream comprises:

introducing the mixed xylene stream into a first adsorptive separation unit and forming a first extract fraction and a first raffinate fraction;

feeding the first extract fraction to a first extract column and forming an extract overhead stream and a extract bottoms stream;

introducing the extract overhead stream to a finishing column which separates the extract overhead stream into the first para-xylene enriched stream and a toluene stream;

feeding the first raffinate fraction to a first raffinate column and forming the first raffinate stream and a raffinate bottoms stream; and recycling the extract bottoms stream and the raffinate bottoms stream to the first adsorptive separation unit.

14. The process of claim 13 wherein introducing the isomerization reactor product stream into the second separation assembly and producing the second para-xylene enriched stream and the second raffinate stream comprises:

introducing the isomerization reactor product stream into the second adsorptive separation unit and forming a second extract fraction and a second raffinate fraction;

feeding the second extract fraction to a second extract column and forming a second extract overhead stream and the second para-xylene enriched stream;

feeding the second raffinate fraction to a second raffinate column and forming a second raffinate overhead stream and the second raffinate stream; and recycling the second extract overhead stream and the second raffinate overhead stream to the second adsorptive separation unit.

15. The process of claim 14 further comprising:
dividing the second raffinate stream into a first portion as the drag stream and a second portion;
introducing the first portion of the second raffinate stream into an aromatic conversion unit and producing a second mixed aromatic stream;
introducing the second mixed aromatic stream into the xylene fractionation unit; and
introducing the second portion of the second raffinate stream into the isomerization unit.

16. The process of claim 9 wherein
introducing the mixed xylene stream comprising the plurality of xylene isomers into the first separation assembly and producing the first para-xylene enriched stream and the first raffinate stream comprises introducing the mixed xylene stream and a first desorbent stream into a first adsorptive separation unit disposed within the first separation assembly; and
introducing the isomerization reactor product stream into the second separation assembly and producing the second para-xylene enriched stream and a second raffinate stream comprises introducing the isomerization reactor product stream and the second desorbent stream into a second adsorptive separation unit disposed within the second separation assembly, wherein the first desorbent stream differs from the second desorbent stream.

17. The process of claim 1 wherein;
introducing the mixed xylene stream comprising the plurality of xylene isomers into the first separation assembly comprises introducing the mixed xylene feed stream and a first desorbent selected from the group consisting of para-diisopropylbenzene and tetralin into a first adsorptive separation unit disposed within the first separation assembly; and
introducing the isomerization reactor product stream into the second separation assembly comprises introducing the isomerization reactor product stream and toluene into a second adsorptive separation unit disposed within the second separation assembly.

* * * * *